United States Patent
Kerns

(10) Patent No.: US 11,643,407 B2
(45) Date of Patent: May 9, 2023

(54) INDANES AS NRF2 ACTIVATORS

(71) Applicant: GLAXOSMITHKLINE INTELLECTUAL PROPERTY DEVELOPMENT LIMITED, Brentford (GB)

(72) Inventor: Jeffrey K. Kerns, Collegeville, PA (US)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 165 days.

(21) Appl. No.: 17/056,495

(22) PCT Filed: May 16, 2019

(86) PCT No.: PCT/IB2019/054607
§ 371 (c)(1),
(2) Date: Nov. 18, 2020

(87) PCT Pub. No.: WO2019/224667
PCT Pub. Date: Nov. 28, 2019

(65) Prior Publication Data
US 2021/0198249 A1 Jul. 1, 2021

Related U.S. Application Data

(60) Provisional application No. 62/675,247, filed on May 23, 2018.

(30) Foreign Application Priority Data

Jun. 7, 2018 (IT) .................... 102018000006105

(51) Int. Cl.
C07D 417/10 (2006.01)
C07D 249/04 (2006.01)
A61K 9/00 (2006.01)

(52) U.S. Cl.
CPC ......... *C07D 417/10* (2013.01); *C07D 249/04* (2013.01); *A61K 9/0019* (2013.01); *A61K 9/0053* (2013.01)

(58) Field of Classification Search
CPC .................... A61K 31/5513; C07D 417/10
See application file for complete search history.

(56) References Cited

U.S. PATENT DOCUMENTS 10,272,095 B2 * 4/2019 Kerns .................. C07D 403/06
10,485,806 B2 * 11/2019 Kerns .................. C07D 498/04

FOREIGN PATENT DOCUMENTS

WO  WO 2015/092713 A1  6/2015
WO  WO 2016/203400 A1  12/2016
WO  WO 2016/203401 A1  12/2016

* cited by examiner

*Primary Examiner* — Rei Tsang Shiao
(74) *Attorney, Agent, or Firm* — Nora L. Stein

(57) ABSTRACT

The present invention relates to indane compounds, methods of making them, pharmaceutical compositions containing them and their use as NRF2 activators. In particular, the invention relates to compounds of Formula (I) or Formula (II), and pharmaceutically acceptable salts thereof:

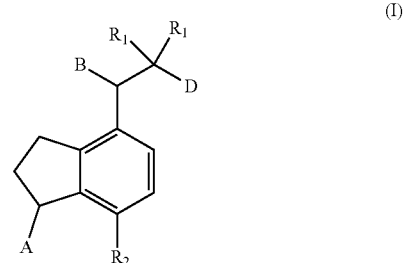

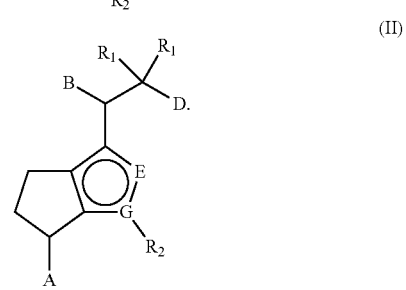

8 Claims, 3 Drawing Sheets

INDANES AS NRF2 ACTIVATORS

This application is a § 371 national phase entry of International Application No. PCT/IB2019/054607, filed May 16, 2019, which claims the benefit of U.S. Provisional Application No. 62/675,247, filed May 23, 2018.

FIELD OF THE ART

The present invention regards the field of hardware/software combined systems for certifying processes. More in detail, the method subject of the invention regards the field of permissions and request for easements functional towards laying down infrastructures for service networks and it aims at optimising the times for the management of a document in all processing steps involved in obtaining the required authorisations. Even more specifically, the documents in question are those regarding piling for laying down service networks preferably of the aerial type.

PRIOR ART

The widespread availability of service networks is a crucial requirement in any developed town nowadays. The aerial component for distributing these networks cannot do without piling.

It often happens that the positioning of the piles falls within private land or other restricted areas and the construction thereof requires authorisation by the public administration or by other due authorities or even private individuals coordinating several due territorial departments to obtain several authorisations required for each pile to be erected.

Up to date, a similar procedure requires, especially in Italy, extremely long technical times and thus even more financial burden for the service manager interested in building the network.

Currently, the bureaucratic process is strictly managed at paper level, with authorisation contracts signed and countersigned by the parties in question on paper.

It is clear that the digitisation of the entire process is currently indispensable even with the aim of preventing and discouraging possible abuse, corruption to obtain permissions and similar unlawful conduct, that a digital system, in which all documents would be available for view in total transparency, would detect immediately.

At an industrial patent level there does not seem anything capable of attaining the object of overcoming the aforementioned criticalities.

Some patents regard similar processes such as for example the Chinese patent no CN104008460, which claims a method for issuing a legal document regarding vehicle licensing certificates in a digitised manner. The uniqueness of registration certificates is recognised through serial numbers issued by the designated Ministry. The advantages of the method lie in the fact that the authorisation of the serial numbers at the cryptography is carried out on registration certificates and prevents the registration certificates from being printed, copied and utilised repeatedly unlawfully. As a matter of fact, the use of the information subject of the registration certificates is shared using a complete application platform for managing the data traffic of the Ministry and inventory of the registration certificates of all vehicles.

Another patent, patent no CN 103761600, refers to the field of e-government platforms regarding the cryptography. The platform comprises several safety and authentication levels for the operators who grant or deny authorisation to operations and have the advantage of improving the safety and efficiency of the government bureaucratic machine.

As for now the state of the art does not seem to reveal any hardware/software application which, as concerns systems aimed at making the public authorisation process leaner and aimed at building pile-borne networks.

The problem with this type of infrastructures lies in the need for coordinating at several levels (government-regional-provincial-municipal) which arises from the need of expanding the network.

Thus, an object of the present invention is to provide a method to be implemented by means of special hardware devices, which allows to obtain the authorisations for piling works and the certificate of compliance with the works carried out.

DESCRIPTION OF THE INVENTION

Described according to the present invention is a method that allows to obtain authorisations from the due authorities and verification of compliance with the works carried out upon approval of the project for building pile-borne aerial networks, effectively solving the problems outlined above.

The planning organisation consists of the following subjects, in decreasing hierarchical and responsibilities scale: administrator; managers; authorities; technicians.

Each technician will advantageously be provided with tools that allow the technician to perform the duty thereof in a recorded and certifiable manner in which each single step is advantageously stored in the memory of a dedicated server. Such devices are at least:
   a portable electronic device, geolocated and connected to the internet, i.e. a tablet or a smartphone on which an App dedicated to the system is downloaded and installed in advance;
   at least one positioning tool for example a peg for indicating the location of the pile so as to be able to geo-reference the position thereof with relative photo.

In a preferred embodiment of the present invention, the kit given to the technician who materially executes the work contains a plurality of positioning tools (pegs) provided with geolocation sensors and preferably even with inertial sensors.

After obtaining the signatures and the various authorisations that will be further examined hereinafter, when the technician drives the positioning tool into the ground to identify the location of the future pile, the latter starts to send to any data storage system, for example a common dedicated server, the data regarding the geographic position thereof. Should there be detected a change of position not previously authorised by the technician, the system generates an alarm which will be notified on the electronic devices of all the involved subjects in that specific piling project.

Possibly even a further alarm will be sent in case of an attempt to tamper with or accidentally damage the positioning tool detected by the inertial sensor incorporated therein.

Advantageously, besides the technicians even the other subjects (administrator, managers, authorities) who take part in the system are provided with their own electronic devices connected to the internet, previously downloaded and installed on which is the App which serves as communication interface between all these subjects and the dedicated server (or another data storage system) stored in whose memory are all required documents in electronic format and available for vision according to specific authorisations.

Advantageously, each regional manager can monitor and organise the work of a number of technicians suitably distributed depending on the size of the documents to be handled. This number could grow should the modifications to be made to the layouts, with respect to the initial plan, become too many and such to affect the documents permits and validation issuance times. The document consists in verifying the feasibility and obtaining permits for one or more pile-borne aerial sections in the territory of competence of each manager.

The process subject of the present invention starts with a first step for allocating the document consisting of the following steps:
 planning per processing steps and geographic areas of the project to be implemented;
 allocating the document to a manager.

Once through with the document allocation step, carried out by the administrator, the processing step, carried out by the regional manager, begins.

After viewing the documents, by means of the electronic device thereof connected to the internet, the manager takes over the documents to indicate the beginning of the processing and the commencement of the work is automatically notified to the administrator.

One of the main advantages of the present invention lies in the traceability, in real time, of all processing steps from the date of allocation to the process validation date.

The managers have the task of distributing the assignments to the various available technicians and monitoring the state of progress of the process for compliance with the times and budget set by the administrator.

The execution of the work documents by the technician, which occurs during the actual processing step, consists in retracing and setting an appointment with the single subjects owners of the land subject of the project. When surveying the land, one has to identify the future position of the pile of the designed network and drive the positioning tool given thereto into the ground. Should the tool be of the simple type, i.e. not provided with a geolocation sensor incorporated thereinto, the technician must take a geo-referenced photo, by means of the electronic device given thereto, so as to advantageously send the exact data of the pile position to the dedicated server.

In a preferred embodiment of the present invention, the portable electronic device, connected to the internet and geolocated, of the technicians is connected to at least one video camera that can be worn by the technician so as to keep trace of the relative video data in the memory when inserting the peg or the positioning tool and signing the permits by the owner of the land subject of piling.

Another objective of the technician during this step of executing the task is to obtain the signature, preferably digital by means of a common electronic pen given to the technician, of the owner of the land to obtain the permit.

Advantageously, all the processing steps of the technician will be uploaded, in real time, on the App, stored in the memory of the dedicated server and made accessible to all subjects in question with access to said App.

During the processing the technician may communicate to the manager any information or remarks to the works, in automatic mode, by means of a special function of the App. In case of failure to obtain permits for some piles or should there arise the need, due to various reasons, to change the layout provided for at the planning stage, the technician may advantageously contact one of the persons under the authority of the manager.

Advantageously, should the process be suspended for any reason, the documents will move on to "SUSPENDED" mode. When the hindrance to proceeding with the document ceases, the technician may advantageously, by means of said App, press the "END OF SUSPENSION" button thus determining the continuation of the processing step.

Advantageously, for each processed document, excluding the time span in which the document was left suspended the dedicated server keeps count of the dedicated hours for periodically extrapolating statistics regarding the efficiency of the technician who processed them.

Another case of impossibility to process the document could arise from unresolvable problems such as for example the infeasibility of the layout, inaccessibility of the land and the like. In these cases, the technician communicates the "non-processability" of the document and re-transmits to the manager to carry out a new planning step and subsequent reallocation.

Should the technician successfully obtain the permits, there directly follows the closure of the document with the uploading of the documents in the relative folder of the memory of the dedicated server and pressing the "END OF DOCUMENT" button.

In case of negative result regarding the obtainment of the permits, the technician may carry out a step for proposing a new layout so as to overcome the problem. Should the new layout be accepted by the manager, the technician proceeds with the new processing to obtain permits.

Upon communicating the "END OF DOCUMENT", the document, complete with obtained permits, support documents, ownership indemnity documents and possible notes, is handed back to the manager who will carry out the relative verification and validation request, unless there are grounds for re-processing or an invalidation, in which case the document will be reallocated or invalidated by the manager.

In case of positive validation outcome, the document is closed and stored, saving each executed step in a relative folder of the memory of the dedicated server. In case of negative validation outcome, the national administrator immediately notifies the manager in question who will see to, within the authority thereof, reprocessing the document within the times agreed upon starting from a new allocation step.

The cycle of a document terminates with the validation activity carried out by the administrator. The "VALIDATED" status is attributed by the administrator after verifying whether what was proposed by the manager correctly corresponds to the official and substantial requirements for laying down the piles the planned or re-planned layout.

The App will advantageously offer the various levels of the project organisation the possibility to have a customised interface, by means of a dedicated appliance.

The appliance levels will preferably be four, aligned with the parties involved in the project organisation, each one of which will offer the possibility of access to the portal and use the tools dedicated for the appliance. Advantageously, fixed or engraved on each built pile will be the reference number or identification code of the document stored in the memory of the dedicated server.

The advantages provided by the present invention will be clear in light of the description outlined up to now. Furthermore, they will be more apparent due to the attached figures and relative detailed description.

DESCRIPTION OF THE FIGURES

The invention will be described hereinafter in at least one preferred embodiment, provided by way of non-limiting illustration, with reference to the attached figures, wherein.

DETAILED DESCRIPTION OF THE INVENTION

Now, the present invention will be illustrated purely by way of non-limiting or non-binding example, with reference to the figures illustrating some embodiments regarding the present inventive concept.

Figure 1:
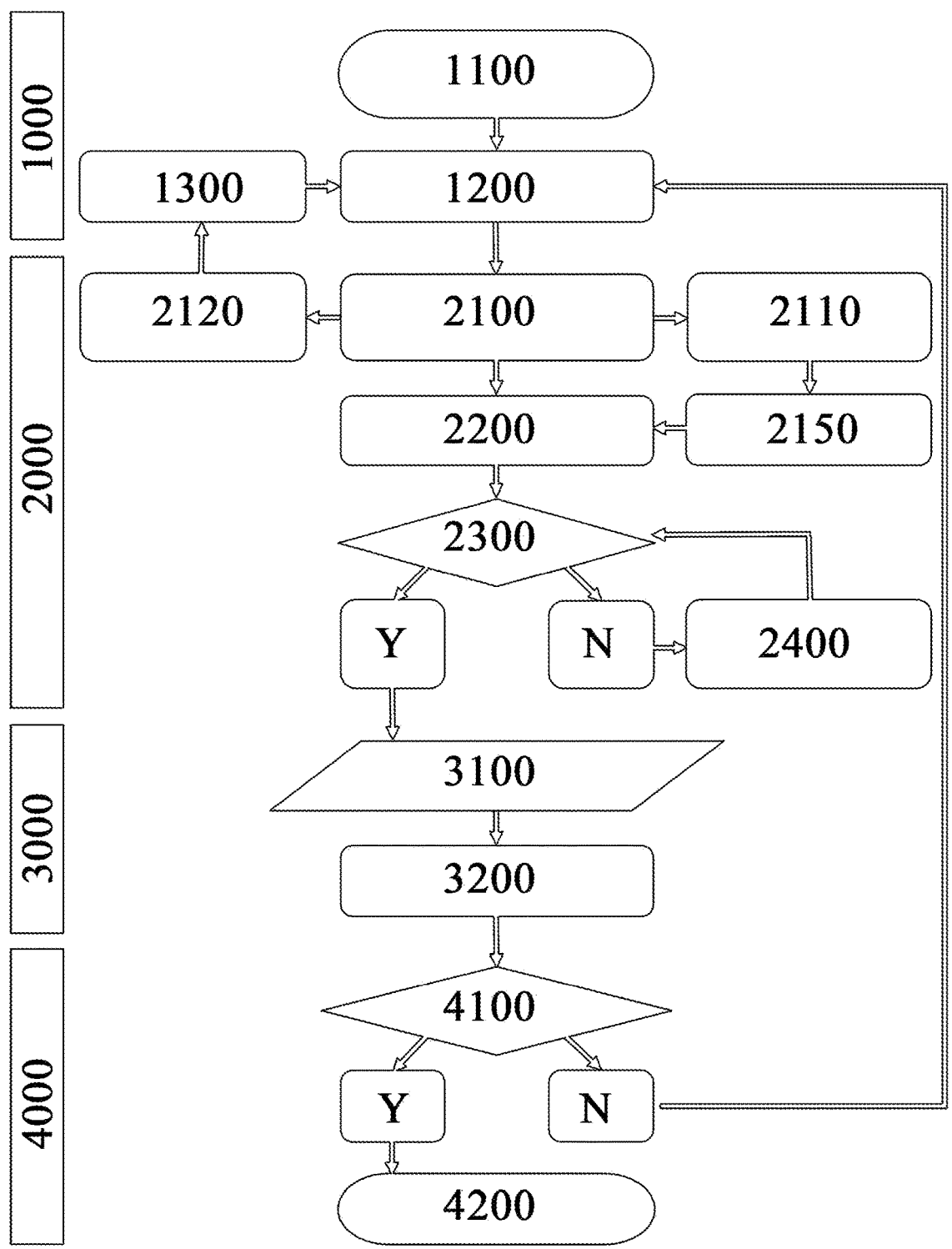
FIG. 1 shows the flow chart subject of the method for obtaining the permits subject of the present invention.
Figure 2:
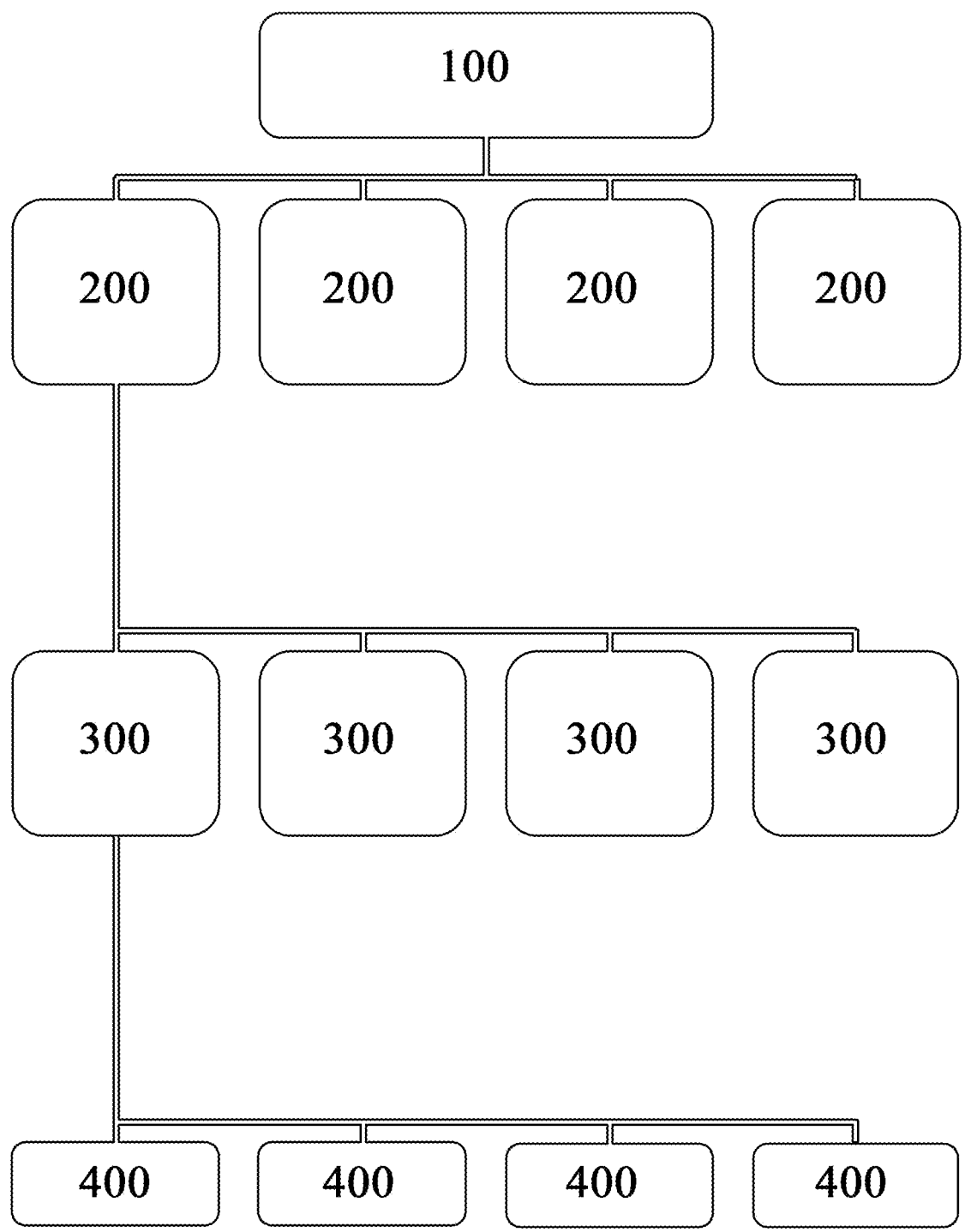
FIG. 2 shows the hierarchical diagram and the territorial authority of the various subjects that contribute to the implementation of the method.
Figure 3:
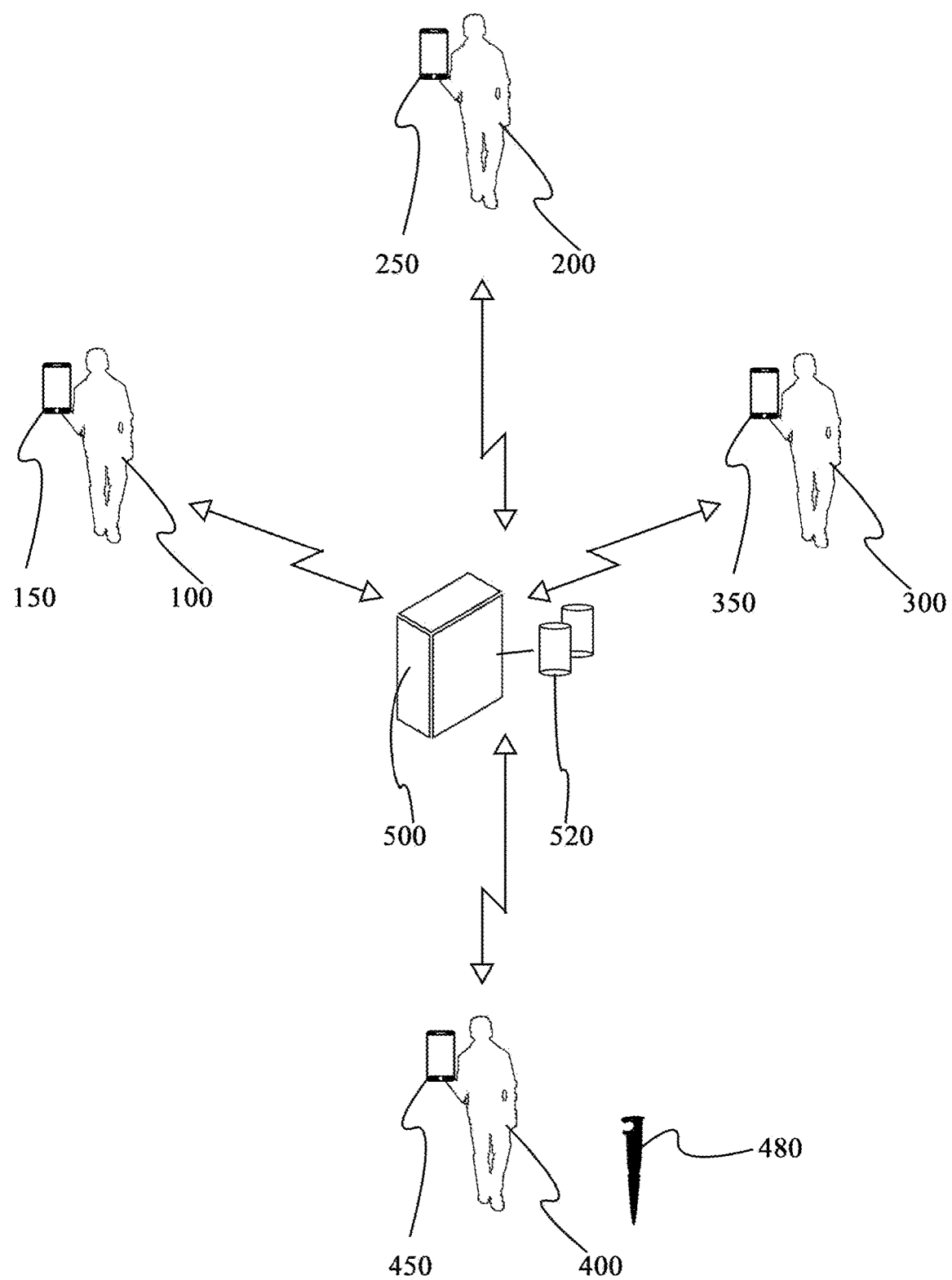
FIG. 3 illustrates a block diagram of the subjects and the hardware components that are interfaced in the implementation of the method subject of the invention.

With reference to FIG. 1 shown is a method of the present invention in the embodiment thereof, deemed as the best up to date, which is implemented as follows.

As concerns the management of a project at national level, an organisation of personnel with territorial authority capable of being able to obtain the permits required to execute the project within the required pre-set times was provided for.

Such organisation consists of the following subjects, in hierarchical scale:
- at least one national administrator 100;
- a plurality of regional managers, directly under the supervision of said national administrator 100;
- a plurality of provincial authorities, each one of whom are under the supervision of a reference regional manager 200, who must be of an appropriate number depending on the extensiveness of the area of authority of the regional manager who supervises them;
- a plurality of technicians, each one of whom under the supervision of the reference provincial manager 300, who must be of an appropriate number depending on the number of permits to be obtained.

In order to perform the duties thereof, each technician 400 will be provided with tools that allow him to handle the tasks thereof to the best of abilities thereof and as precisely as possible:
- a portable electronic device 450, geolocated and connected to the internet;
- at least one peg 480 for indicating the positioning of the pile so as to be able to carry out the position referenced geolocation thereof with the relative photo.

Besides the technicians 400, even the other subjects who take part in the system are provided with their own electronic devices 150-250-350 connected to the internet, previously downloaded and installed on which is the App which serves as communication interface between all these subjects and the dedicated server 500 stored in whose memory 520 are all required documents in electronic format and available for view according to specific authorisations.

Each process step described hereinafter is carried out by the electronic devices of the involved subjects by means of the dedicated App, leaving trace of each step in a relative work folder stored in the memory 520 of the dedicated server 500.

The process subject of the present invention starts with a first step 1000 for planning the processing steps and for the geographic areas of the project to be carried out. This step is carried out independently by the national administrator 100 who firstly carries out the organisation step 1100 and, subsequently the allocation 1200 to a regional manager 200. The document will consist in verifying the feasibility and obtaining permits for one or more pile-borne aerial sections in the territory of competence of the regional manager 200.

Each allocated document contains all information required to carry out the work:
- names of the Provinces in which the Municipalities to be addressed are located;
- name of the Municipalities;
- layouts of the geo-referenced piling lines showing the relative cadastre parcels subject of permit request;
- names of the owners of the cadastre parcels subject of piling;
- deadline by which the permit request must be completed;
- budget available for possible indemnity to the owners;
- budget for the work to be carried out;
- number of permits to be obtained depending on the layouts scheduled during planning;
- reference of the national administrator 100 who commissioned the document.

once through with the document allocation step 1200, by the national administrator 100, the execution step 2000 carried out by the regional manager 200 begins.

Once through with the computer portal (App) authentication operations, the latter receives the list of documents to be processed in the "ALLOCATED" status, to which the regional manager can access through the portal to view, print or download, for local management. Indicated for each document is the number of layouts, the scheduled timeline and the target date for obtaining the permits. This information is required for identifying the processing priority to be applied by the regional manager 200.

The national administrator 100 reserves the right to revoke the documents allocated to the regional managers 200 for contract reasons (e.g. submission delay, submission of substandard documents, etc.).

In the display screen of the manager's App, the revoked document is positioned under "CANCELLED" status, with an automatic notification to the regional manager 200, preferably by email.

Upon viewing the documents, the regional manager 200 executes the "TAKE OVER" 2100 of the documents to indicate the commencement of the processing, with ensuing calculation of processing hours, and the national administrator 100 is notified about this through the App.

More in detail, through the App the regional manager 200 may see the list of documents marked by the respective processing status which may be:
- "Allocated";
- "Taken Over", with relative date;
- "Suspended", stating the grounds for suspension;
- "Terminated" or "Validated" indicating the date for each municipality.

The main activities of the regional managers will be:
- implementation and compliance with all project deadlines set by the national administrator 100;
- monitoring the state of progress of the works of the regions taken over;
- monitoring the state of progress of the works of the documents;
- monitoring the issuance of permits;
- monitoring the budget for indemnity to private individuals, regarding the documents taken over.

The regional manager 200 also has the operations centre service management duties operating as a help desk, providing the technicians with the best advice on the "ground". Specifically, the regional manager performs the following activities:

monitoring the state of progress of the works of the Municipalities/documents under management;
monitoring the state of progress of the works of the documents;
monitoring the issuance of permits;
advice to technicians 400 for support on identifying a new alternative applicable layout;
project proposals and suggestions for the single Municipalities and documents.

The actual processing step 2200 is carried out by a technician 400 employed by the regional manager 200 who took the document over, and consists in:
tracing the single owners;
Setting an appointment;
identifying the pile by means of the electronic device 450 provided for geo-location purposes;
driving the provided peg 480 into the ground and subsequent geo-referenced photo;
permit and attachments signing step 2300;
uploading information onto the App 3100, in a document closing step 3000, in case of positive outcome Y of the previous permit obtainment step 2300.

Should the land have been allocated, it will be necessary to trace the owner and obtain a proxy from a trusted person thereof or the lessee for authorisation to sign permits.

The permit will be drafted like and have the validity of a contract and indicate:
the identification data of the signer;
Reference to the parcel and position of the pile/s subject of reference of the permit with respect to the layout prepared during planning;
any identification data of the proxy if the signer is not the owner;
the details of the identification document thereof;
the attachment with the excerpt of the map.

In order to proceed to said step 3000 for closing the processing on the App, the technician 400 must open a processing folder, which will contain the following information:
the references of the signer;
the signed permit document;
the documents of the signer;
an attachment with the map;
the affidavit of the signer;
the indemnity form (if present) which will be provided for the installation of the pile;
the geo-referenced photo of the peg 480 to identify the exact position of the pile on the map.

During the processing the technician 400 may communicate to the manager any information or remarks to the works, in automatic mode, by means of the "processing remarks" function of the App.

Should the permit obtainment step 2300 be unsuccessful N, the technician 400 must contact the provincial managers 300 connected to the same regional manager 200 so as to change the layout 2400 and thus a new attempt to obtain the permits 2300. The alternative route must be examined and approved by the regional manager 200.

Should the processing have been suspended "due to reasons not attributable to the technician 400" (the owner fails to show up at the appointment, complex work, requested/expected permits and authorisations, other causes . . . ) the "SUSPENSION" 2110 AND "END OF SUSPENSION" 2150 steps on the App allow the technician 400 to notify the regional manager 200 that the documents is temporarily suspended, stopping the processing time count (work hours).

The technician 400 must also communicate the date and time of suspension, the grounds, the time expected to solve the problem and any remarks.

If he cannot take action independently so as to obtain the permits 2300 (for example: infeasible layout, failure to obtain the permits, lack of feasible alternatives etc.) the technician 400 must code the document as "NOT PROCESSABLE" 2120 and it will be returned to the regional manager 200 for possible re-planning 1300 and subsequent reallocation 1200.

The documents closing step 3000 occurs at two levels: single and shared.

Upon completing the permit request process for all elements, the technician 400 must update the status of the documents regarding the Municipality in charge.

Using the App, the technician 400 must communicate the "END OF DOCUMENT" 3200 and thus the completion of the whole processing of the following information:
permits obtained (yes/no/percentage of obtained permits);
support documents (geo-referenced photo, other);
documents for the indemnity of the owners;
possible notes.

The document 3200 can be closed by the technician 400 only once the relative fields of all elements of the document will have been filled in on the App.

Upon communication of the "END OF DOCUMENT" 3200, the document will be returned to the regional manager 200 who will carry out the verification step 4000 through a validation request step 4100 (certificate), unless there are grounds for having the processing redone or nullified, in which case the document will be reallocated or nullified by the regional manager 200.

All status changes must also contain the date data when the processing was carried out.

The cycle of a document terminates with the validation activity 4100 carried out by the national administrator 100. The "VALIDATED" status 4200 is attributed by the national administrator 100 after positively Y verifying 4100 whether what was proposed by the manager correctly corresponds to the official and substantial requirements for laying down the piles on the planned or re-planned layout.

In case of negative outcome N of the verification, the national administrator 100 immediately notifies the regional manager 200 in question who will see to, within the authority thereof, reprocessing the document within the times agreed upon.

The document reallocated to the same regional manager 200 is considered as new in the interface of the App also maintaining the same date of the initial allocation as the date of the previously negatively validated document and considering the date of allocation of the negatively validated document for calculating the service fees.

The App will offer the various levels of the project organisation the possibility to have a customised interface, by means of a dedicated appliance.

The appliance levels will be four, aligned with the parties involved in the project organisation, each one of which will offer the possibility of access to the portal and use the tools dedicated for the appliance.

From the App interface point of view the system must allow the technician 400 to have evidence on:
the allocated documents and the relative times and dates of delivery set by the organisation of the territorial coordination regional manager 200 based on the deadlines set by the national administrator 100;
graphic interface of the layout and of the single piles, with the possibility of adding photographic support material;

cadastre parcels intersected by the layout;
the list of owners of the parcels on which the elements subject of the document lie;
the interface for adding new layouts;
the possibility of being able to add appointments and references for the owners;
the documents regarding the permits, with the possibility of uploading on the database;
the possibility of adding remarks on the layout and on the document.

From the App interface point of view, the system must allow the provincial manager 300 to have evidence on:
the allocated documents currently under processing, regarding which the GANTT chart prepared by the organisation of the territorial coordination regional manager 200, based on the deadlines set by the administrator, must also be available;
the technician 400 subject of allocation of the single document who is the provincial manager 300 manages;
the state of progress of the project, in terms of the obtained permits Municipality by Municipality with respect to the schedule laid down by the GANTT chart;
the costs accrued at the date of viewing (possible indemnities);
the number of changes to the layouts scheduled at the planning step;
the suspended taken over documents and the grounds for suspension;
the nullified taken over documents and the grounds for nullification.

From the App interface point of view, the system must allow the regional manager 200 to have evidence on:
the allocated documents under processing regarding which the GANTT chart must be prepared based on the deadlines set by the national administrator 100;
the provincial manager 300 and the technician 400 subject of allocation of the single documents who is the regional manager 200 manages;
the state of progress of the project, in terms of the obtained permits Municipality by Municipality with respect to the schedule laid down by the GANTT chart;
the costs accrued at the date of viewing (fee to the territorial organisation, indemnities, etc.);
the number of changes to the layouts scheduled at the planning step;
the suspended taken over documents and the grounds for suspension;
the nullified taken over documents and the grounds for nullification.

From the App interface point of view, the system must allow the national administrator 100 to have evidence on:
the documents under processing for all regional managers;
the regional manager 200, the provincial manager 300 and the technician 400 subject of allocation of the single document;
the state of progress of the project, in terms of the obtained permits Municipality by Municipality with respect to the schedule laid down by the GANTT chart;
the costs accrued at the date of viewing (fee to the territorial organisation, indemnities, etc.);
the number of changes to the layouts scheduled at the planning step;
the suspended documents and the grounds for suspension;
the nullified documents and the grounds for nullification.

Lastly, it is clear that the invention described up to now may be subjected to modifications, additions or variants obvious to a man skilled in the art, without departing from the scope of protection outlined by the attached claims.

The invention claimed is:
1. A compound of Formula (II):

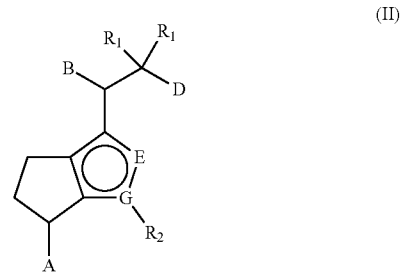

(II)

wherein:
B is benzotriazolyl, phenyl, triazolopyridinyl, —O—$(CH_2)$-triazolyl, or —$(CH_2)_2$-triazolyl wherein each of benzotriazolyl, phenyl, triazolopyridinyl, —O—$(CH_2)$-triazolyl, or —$(CH_2)_2$-triazolyl is unsubstituted or substituted by 1, 2, or 3 substituents independently selected from —$C_{1-3}$alkyl, —O—$C_{1-3}$alkyl, —CN, —$(CH_2)_2$—O—$(CH_2)_2$—$OR_3$ and halo;
D is —C(O)OH, —$C(O)NR_3R_4$, —$C(O)NHSO_2CH_3$, —$SO_2NHC(O)CH_3$, —S-(trifluoromethyl)-4H-1,2,4-triazol-2-yl, —$NR_3$—C(O)—$R_4$, —$NR_3$—C(O)—$NR_3R_4$; —$NR_3$—C(O)—O—$R_4$ or tetrazolyl;
$R_1$ is independently hydrogen, —$C_{1-3}$alkyl, F, —$C_{3-6}$spirocycloalkyl, oxetane, or the two $R_1$ groups together with the carbon to which they are attached form a cyclopropyl group;
$R_2$ is hydrogen, methyl, —$CF_3$, or halo;
$R_3$ is hydrogen or —$C_{1-3}$alkyl;
$R_4$ is hydrogen, —$C_{1-5}$alkyl, —$C_{3-7}$cycloalkyl, —$C_{4-8}$heterocycloalkyl, —$C_{1-5}$alkoxy, —$C_{1-3}$alkyl-O—$C_{1-3}$alkyl, —$C_{1-3}$alkyl-NH—$C_{1-3}$alkyl, —$C_{1-3}$alkyl-$SO_2C_{1-3}$alkyl, —$C_{1-3}$alkyl-$C_{4-8}$heterocycloalkyl, —$C_{1-3}$alkyl-$C(O)NR_4R_5$, aryl or heteroaryl, wherein each of —$C_{1-5}$ alkyl, —$C_{3-7}$ cycloalkyl, —$C_{4-7}$ heterocycloalkyl, —$C_{1-5}$alkoxy, —$C_{1-3}$alkyl-O—$C_{1-3}$alkyl, —$C_{1-3}$alkyl-NH—$C_{1-3}$alkyl, —$C_{1-3}$alkyl-$C(O)NR_4R_5$, aryl or heteroaryl is unsubstituted or substituted by one or two substituents selected from —OH, —$CO_2H$, —$C(O)NR_4R_5$, —$C(O)OR_3$, —N—C(O)—$C_{1-3}$alkyl, F, —CN, —CH—$F_2$, —$CF_3$, —$(CH_2)_n$—O—$(CH_2)_m$—$CH_3$, —$C_{3-7}$cycloalkyl and a 5-6-membered heteroaryl ring containing 1, 2 or 3 heteroatoms selected from O, N and S;
or $R_3$ and $R_4$ together with the nitrogen atom to which they are attached form a 5-8-membered heterocyclic ring, an 8-11-membered bicyclic heterocyclic ring or a 9-10-membered bridged bicyclic heterocyclic ring, wherein each 5-8-membered ring, 8-11-membered bicyclic ring, or 9-10-membered bridged bicyclic ring optionally includes one —C(O) or one —$S(O)_2$, and wherein each 5-8-membered ring, 8-11-membered bicyclic ring, or 9-10-membered bridged bicyclic ring optionally contains one, two or three oxygen ring atoms, one, two or three sulfur ring atoms or one, two or three nitrogen ring atoms, and wherein each 5-8-membered ring, 8-11-membered bicyclic ring, or 9-10-membered bridged bicyclic ring is unsubstituted or substituted by one, two or three substituents independently selected from —$C_{1-5}$alkyl, —$C_{3-7}$cycloalkyl, —C$_{4-7}$heterocycloalkyl, —(CH$_2$)phenyl, halogen, —NR$_3$R$_5$, —CHF$_2$, —CF$_3$, and —(CH$_2$)$_n$—O—(CH$_2$)$_m$—CH$_3$;

A is tetrahydrobenzoxazepinyl, tetrahydro-pyrido-oxazepinyl, piperidinyl, tetrahydrobenzazepinyl, phenyl, tetrahydropyrrolopyrazinyl, imidazopyridinyl, tetrahydrobenzodiazepinyl, piperidopyrimidinyl, dioxidotetrahydrothiophenyl, tetrahydroimidazodiazepinyl, oxazepane or morpholinyl;

wherein each of tetrahydrobenzoxazepinyl, tetrahydropyrido-oxazepinyl, piperidinyl, tetrahydrobenzazepinyl, tetrahydropyrrolopyrazinyl, imidazopyridinyl, tetrahydrobenzodiazepinyl, piperidopyrimidinyl, dioxidotetrahydrothiophenyl, tetrahydroimidazodiazepinyl, oxazepane or morpholinyl is unsubstituted or substituted by 1, 2, or 3 substituents independently selected from —C$_{1-3}$alkyl, —C$_{3-6}$spirocycloalkyl, halo, —CN, —O—C$_{1-3}$alkyl, —CH$_2$—O—CH$_3$, and —OH;

and wherein the oxazepane is further unsubstituted or substituted by 1 or 2 substituents independently selected from —C$_{1-3}$alkyl and —C$_{3-7}$cycloalkyl;

and wherein the morpholinyl is further unsubstituted or substituted by phenyl which phenyl is unsubstituted or substituted by a substituent independently selected from —C$_{1-3}$ alkyl and —O—C$_{1-3}$ alkyl;

or A is

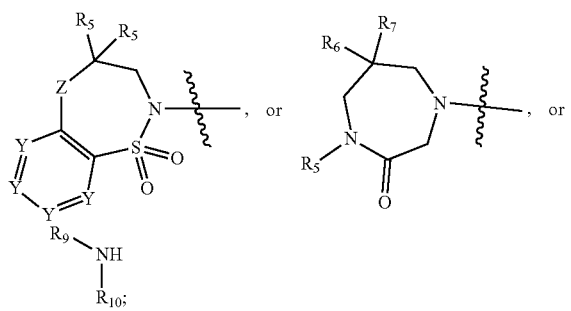

Y is independently selected from N or CH;
E is independently S, O, N;
G is independently C, N;
Z is O, CH$_2$, NR$_5$, S, S(O) or S(O)$_2$;
R$_5$ is independently selected from hydrogen or —C$_{1-4}$alkyl;
R$_6$ is hydrogen, —C$_{1-5}$alkyl or —(CH$_2$)$_m$—C$_{3-5}$cycloalkyl;
R$_7$ is hydrogen or —C$_{1-4}$alkyl;
or R$_6$ and R$_7$, together with the carbon to which they are attached form a C$_3$-C$_5$-membered cycloalkyl ring;
and, wherein when A is

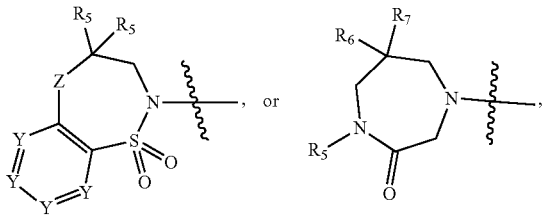

it is unsubstituted or substituted with one, two or three substituents independently selected from halo, —CF$_3$, —C$_{1-4}$alkyl, —CN, —OMe, —C(O)NH$_2$, —OCF$_3$ and —C$_{1-4}$alkylNR$_7$R$_8$;

R$_8$ is —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl, wherein each of —C$_{1-3}$alkyl, aryl, heteroaryl, —C(O)C$_{1-3}$alkyl, —SO$_2$C$_{1-3}$alkyl, —C(O)aryl, —C(O)heteroaryl, —SO$_2$aryl, —SO$_2$heteroaryl, —C$_{3-7}$cycloalkyl, —C$_{1-3}$alkylC$_{3-7}$cycloalkyl, —C$_{1-3}$alkylC$_{3-7}$heterocycloalkyl, —C$_{1-3}$alkyl-heteroaryl or —C$_{1-3}$alkyl-aryl is unsubstituted or substituted by 1, 2 or 3 substituents independently selected from halo, —CN, —CF$_3$, —OCF$_3$, —OCH$_3$, —C$_{1-3}$alkyl, —OC$_{1-3}$alkyl, —OC$_{3-7}$cycloalkyl, —OC$_{3-7}$hetercycloalkyl, —O-aryl and —O-heteroaryl;

R$_9$ is hydrogen, —C$_{1-5}$alkyl or —(CH$_2$)$_m$—C$_{3-5}$cycloalkyl;

R$_{10}$ is H, SO$_2$R$_6$, C(O)R$_6$;

m is 0, 1 or 2; and n is 1 or 2; or a pharmaceutically acceptable salt thereof.

2. A pharmaceutical composition comprising a compound, or a pharmaceutically acceptable salt thereof, according to claim 1 and a pharmaceutically acceptable excipient.

3. A method of treating respiratory and non-respiratory disorders, including COPD, asthma, ALI, ARDS, fibrosis, chronic asthma and acute asthma, lung disease secondary to environmental exposures, acute lung infection, chronic lung infection, α1 antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, atherosclerosis, hypertension, heart failure, acute coronary syndrome, myocardial infarction, myocardial repair, cardiac remodelling, cardiac arrhythmias, Parkinson's disease (PD), Alzheimer's disease (AD), Friedreich's Ataxia (FA), amyotrophic lateral sclerosis (ALS), multiple sclerosis (MS), Huntington's disease (HD), spinal cord injury, traumatic brain injury, ischemic stroke, stroke, Creutzfeldt-Jakob Disease, fatal familial insomnia, Gerstmann-Sträussler-Scheinker syndrome, and related prion diseases, progressive supranuclear palsy, chronic traumatic encephalopathy (CTE), neurodegeneration, dementias, frontotemporal dementias, tauopathies, retinitis pigmentosa, Pick's disease, Neimann-Pick's disease, amyloidosis, cognitive impairment, inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, and high altitude sickness which comprises administering to a human in need thereof, a therapeutically effective amount of a compound, or a pharmaceutically acceptable salt thereof, according to claim 1.

4. The method according to claim 3 wherein the compound, or a pharmaceutically acceptable salt thereof, is administered orally.

5. The method according to claim 3 wherein the compound, or a pharmaceutically acceptable salt thereof, is administered intravenously.

6. The method according to claim 3 wherein the compound, or a pharmaceutically acceptable salt thereof, is administered by inhalation.

7. The method according to claim 3 wherein the disease is COPD.

8. The method according to claim 3 wherein the disease is heart failure.

* * * * *